United States Patent [19]

Wright, Jr.

[11] 4,038,403
[45] July 26, 1977

[54] BENZOTRIAZOLE OVICIDES AND LARVICIDES

[75] Inventor: Donald Perry Wright, Jr., Pennington, N.J.

[73] Assignee: American Cyanamid Company, Stamford, Conn.

[21] Appl. No.: 623,234

[22] Filed: Oct. 17, 1975

[51] Int. Cl.$^2$ .......................... A01N 9/00; A01N 9/22
[52] U.S. Cl. ................................. 424/269; 260/308 B
[58] Field of Search .......................................... 424/269

[56] References Cited

U.S. PATENT DOCUMENTS

| 3,231,579 | 1/1966 | Pawloski | 424/269 X |
| 3,808,334 | 4/1974 | Dahle | 424/269 |
| 3,833,602 | 9/1974 | Buchel et al. | 424/269 X |

FOREIGN PATENT DOCUMENTS 990,111   4/1965   United Kingdom

Primary Examiner—Allen J. Robinson
Attorney, Agent, or Firm—H. G. Jackson

[57] ABSTRACT

The invention is a method for the control of insects and acarina comprising, contacting the eggs of said pests with an ovicidally effective amount of a benzotriazole compound and a method for the protection of living plants against attack by insects and acarina comprising, applying to the foliage of the plants an ovicidally-pesticidally effective amount of a benzotriazole compound to prevent the hatching of the eggs of the organisms oviposited on the foliage and to prevent eclosion of the nymphs of adults of the organisms feeding on the foilage of said plants.

12 Claims, No Drawings

BENZOTRIAZOLE OVICIDES AND LARVICIDES

BACKGROUND OF THE INVENTION

1. Field of the Invention:

The invention pertains to the chemical pesticide field.

2. Description of the Prior Art:

Derivatives of benzotriazoles have been described and evaluated in the literature as antimicrobials, antimalarials, anti-inflammatory agents, ultraviolet absorbers, optical bleaches and plant growth regulators.

U.S. Pat. No. 3,231,579 (1966) describes and claims 2-[6-(2-propynyloxy)-m-tolyl]-2H-benzotriazole, said to be useful as a pesticide for the control of insects, fish worms, bacteria, fungi, roundworms, beetles, roaches, blight and minnows. However no biological evaluation data are given in this patent except for minnows.

U.S. Pat. No. 3,808,334(1974) discloses isomeric mixtures of N,N-dimethyl-1H-benzotriazole-1-carboxamide and N,N-dimethyl-2H-benzotriazole-2-carboxamide and claims a method for the control of Aphids by using said isomeric mixtures. Evaluation data provided in the patent clearly show that the isomeric mixtures described are almost totally ineffective for the control of other insect or acarid pests. The patent does not suggest the ovicidal-larvicidal activity of the compounds of the present invention.

Co-pending application Ser. No. 490,526 filed July 22, 1974 discloses the compounds useful in the present invention as herbicidally effective agents.

SUMMARY OF THE INVENTION

The invention provides a method for the control of insect and acarid pests of agriculturally important plants, the method comprising contacting the eggs of the pests with an ovicidally effective amount of a 1H-benzotriazole compound of the formula I below:

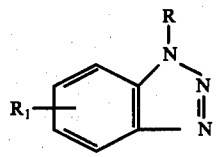

I wherein R is alkyl $C_3-C_8$ straight chain or branched, alkoxy $C_1-C_8$ straight chain or branched, cycloalkyl $C_3-C_8$, cycloalkenyl $C_5-C_6$, mono- or di- $C_1-C_3$ alkylcyclohexyl, cyclohexylmethyl formyloxycyclohexyl, or $-CONR_2R_3$ wherein $R_2$ and $R_3$ are hydrogen or alkyl $C_1-C_4$; and $R_1$ is $-NO_2$ or $-NCS$ and may be in the 4 or 7 position on the benzene ring. The invention also provides a method for the protection of agriculturally important plants against attack by insects and acarids, comprising applying to the plants an ovicidally effective amount of a formula I benzotriazole compound described and defined above, to prevent the hatching of eggs of said pests oviposited on the plants; the ovicidally effective amount of a formula I benzotriazole compound being also sufficient to destroy the larvae, nymphs and adults of the acarids feeding on the plants.

DESCRIPTION OF THE PREFERRED EMBODIMENTS

Among the preferred formula I compounds are those wherein

R of formula I, above, is alkyl $C_3-C_5$ branched, alkoxy $C_1-C_3$ straight chain or branched, $-CON(CH_3)_2$, $C_4-C_6$ cycloalkyl, cycloalkenyl $C_5-C_6$, cyclohexylmethyl; and $R_1$ is $-NO_2$ or $-NCS$.

The most preferred formula I compounds are those wherein

R is from $-C(CH_3)_3$, $-CH(CH_3)(C_2H_5)$,

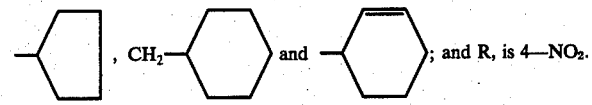

and $R_1$ is 4—$NO_2$.

The above-described benzotriazole compounds of the invention may be prepared by a number of well known routes, some of which are described and graphically illustrated below:

A. A substituted 1H-benzotriazole compound of formula Ia is reacted with an alkylating reagent in a suitable solvent such as acetonitrile, dimethylformamide, dimethoxyethane, dimethyl sulfoxide and the like, in the presence of a base such as sodium or potassium hydroxide or alkoxide at a temperature range of about from 50° C to 100° C for several hours until the reaction is essentially complete:

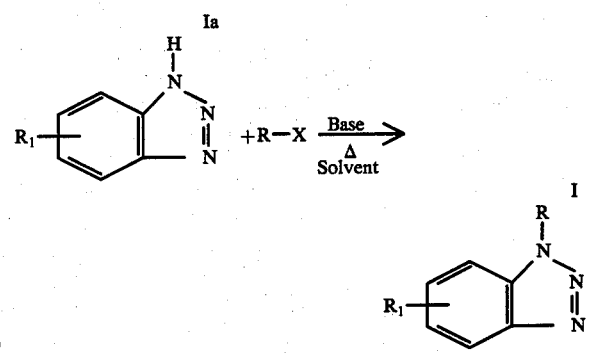

wherein X is halogen, alkylsulfate or p-toluenesulfonate. The above alkylation reaction results in a mixture of the desired formula I compounds and its isomers:

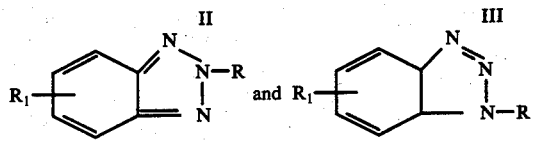

Compound I may then be isolated and purified by standard laboratory procedures such as fractional recrystallizations, chromatography and the like.

B. A substituted 2-chloronitrobenzene is reacted with a primary amine in a 1:2 and preferably in a 1:3 molar ratio at reflux for a period of time ranging from several hours to several days until the reaction is essentially complete. The thus obtained N-substituted 2-nitroaniline is reduced chemically or catalytically to the corresponding diamine from which the desired benzotriazole is obtained by treatment with nitrous acid:

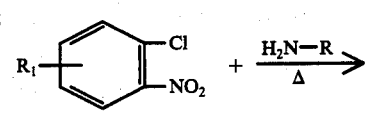

-continued

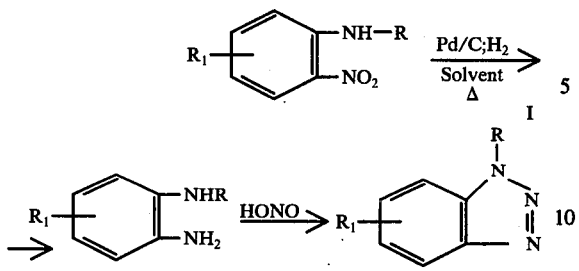

C. When $R_1$ is nitro, the desired compound may be obtained by nitrating the N-substituted benzotriazole precursor in a mixture of concentrated nitric acid and 23% oleum:

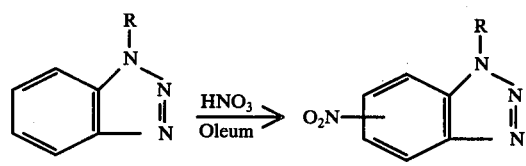

The isolated reaction product is a mixture of isomers from which the desired formula I compound may be isolated by the afore-mentioned laboratory procedures.

Formula I benzotriazole compounds wherein $R_1$ is —NCS and R is as defined above, can be prepared conveniently by a number of routes from the corresponding formula I compounds wherein $R_1$ is nitro.

The common precursor, a formula II benzotriazole compound wherein $R_1$ is amino and R is as hereinabove defined, can be prepared as graphically illustrated and described below:

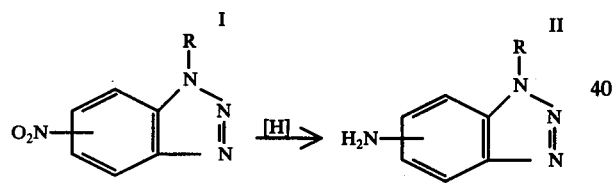

A formula I benzotriazole compound wherein $R_1$ is nitro is reduced chemically e.g. with zinc and hydrochloric acid or with sodium or potassium sulfide in the presence of a $C_1$-$C_3$ alkanol; or catalytically e.g. in a low pressure hydrogenator in the presence of a $C_1$-$C_3$ alkanol and a catalyst such as Pd/C, to yield the corresponding formula II amine.

To obtain the desired formula I compounds wherein $R_1$ is an isothiocyanato group, a formula II amine or an acid addition salt thereof wherein R is as defined above, is reacted with thiophosgene, preferably under anhydrous conditions, e.g. a blanket of inert gas such as nitrogen. The reaction is initially carried out at a temperature between 0° C to 40° C and preferably 10° C to 20° C, and then heated to between about 50° C to 100° C, and preferably to from 60° C to 80° C. The reaction is usually also conducted in the presence of a solvent such as benzene, toluene or xylene.

The isothiocyanates of formula I can be prepared by reacting the appropriate formula II amines with equimolar amounts of carbon disulfide, triethylamine and a carbodiimide represented by the formula: G—N=C=λ N—G wherein G is cyclohexyl, cycloheptyl, alkyl $C_4$-$C_6$ and the like. This reaction is generally conducted in the presence of a solvent such as tetrahydrofuran or an ether such as diethyl ether, at a temperature between about −10° C and +25° C. The above reaction may be illustrated as follows:

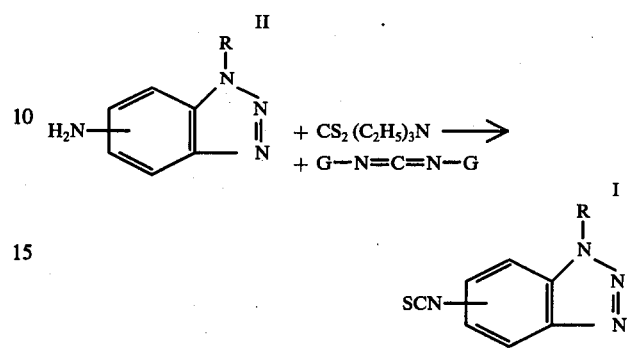

Alternatively the formula I isothiocyanates can be prepared by the reaction of 1,1'-thiocarbonyldiimidazole with formula II aminobenzotriazole in the presence of chloroform at ambient temperature. The reaction may be illustrated as follows:

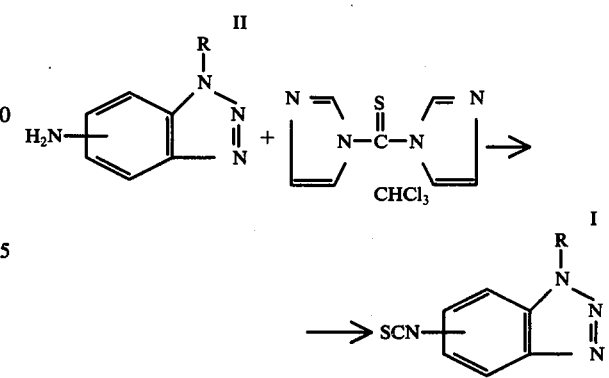

In all of the above depicted reaction sequences R and $R_1$ are as defined above.

For ease of application formula I benzotriazole compounds may be formulated as wettable powders, dusts, dust concentrates, granules or stable dispersions.

Wettable powders can be prepared by grinding and blending from about 50 to 80% by weight of the active compound, an inert carrier such as attapulgite, bentonite, kaolin, talc, diatomaceous earth and the like, about 5% by weight of a dispersing agent such as sodium lignin sulfonate, sodium salts of condensed aryl sulfonic acids and the like; and about 1 to 2% of a wetting agent, such as alkyl aryl polyethylene glycols or dioctyl sodium sulfosuccinate may be added, if so desired.

Dusts and dust concentrates are similarly prepared except that the wetting and dispersing agents are usually omitted from the formulations. Dusts and dust concentrates may contain from about 1 to 99% of active compound.

Granular formulations are prepared by admixing an inert granular substrate with a solution of the active compound in an inert solvent in amounts sufficient to yield a final product containing from about 1 to 30% by weight of active compound. The thus prepared granular formulations may be used wet or may be dried prior to use. If it is of advantage, a wetting agent may also be incorporated in these formulations.

Stable dispersions are prepared by grinding from about 10 to 70% by weight of active compound, a dispersing agent and a wetting agent in an inert solvent, such as water, in a suitable equipment (e.g. ball mill or colloid mill) until a stable dispersion with the desired particle size is obtained. Suitable thickeners, e.g. sodium alginate, hydroxymethyl cellulose and the like may be added if desired.

In practice, wettable powders and stable dispersions are diluted with and dispersed in water to the desired concentration and applied as liquid sprays in sufficient amounts to provide from about 0.14 kg to 5.60 kg per hectare and preferably 0.28 kg to 1.12 kg per hectare of active compound.

This invention is further illustrated by the examples set forth below.

EXAMPLE 1

Evaluation of Broad Spectrum Ovicidal Activity of 1-Substituted-4-nitro-1H-benzotriazole compounds in comparison with Galecron.

Eggs of the following insect and acarid pests are used in these tests:
Tobacco budworm — *Heliothis virescens*
Southern armyworm — *Spodoptera eridania*
Cabbage looper — *Trichoplusia ni*
Mexican bean beetle — *Epilachna varivestis*
Colorado potato beetle — *Leptinotarsa decemlineata*
Malaria mosquito — *Anopheles quadrimaculatus*
P-resistant 2-spotted Spider mite — *Tetranychus urticae*

Eggs for the tests are all selected from laboratory colonies and are always used when 0–24 hours old, except that the potato beetle eggs are field collected. Although the age of these eggs is not known, care is taken to select only bright orange eggs, indicative of relatively recent oviposition. The uniform time of hatch of these eggs demonstrates that most eggs were newly - laid when used.

PROCEDURE

All compounds are formulated as 50% acetone, 50% water solutions at the concentrations given in Table I below.

Except for the mosquito eggs, the appropriate eggs are tested on the substrate upon which they are laid.

The eggs (and substrate) are dipped into the test solutions, agitated for 3 seconds and placed in a hood to dry. When dry, the eggs of the armyworms, loopers, bean beetles and potato beetles are placed in 100 mm diameter petri dishes containing a moist filter paper in the bottom of the dish, the lids are replaced and the petri dishes maintained at 80° F, until the eggs hatch. The tobacco budworm eggs are placed in 8 oz Dixie cups along with a short piece of dental wick saturated with water and a cotton leaf. A clear plastic lid is snapped on and the cups held at 80° F, until the eggs hatch.

In the mosquito egg test 250 ml of test solution is placed in a 400 ml beaker and a wax paper ring floated on the surface. This is to prevent the eggs from floating up the meniscus curve and drying out on the walls of the beaker. About 100 eggs 0–24 hours old are added to the beaker with a screen spoon and the beakers held at 80° F, until the eggs hatch in about 2 days.

Estimates of percent egg kill are made on the day of normal hatch of untreated controls, but all tests are retained an additional 2 days to determine if egg hatch has been delayed beyond normal.

The data obtained are given in Table I.
The following ratings are used:
+ = no hatch
± = partial hatch
0 = 100% hatch Galecron is a product of CIBA - Geigy Corporation and has the following structure:

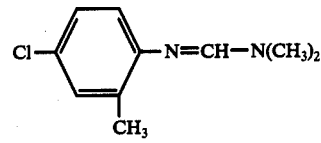

Table I

Ovicidal Activity of 1-Substituted-4-nitro-1H-Benzotriazoles vs. Galecron;
Application rates are given in ppm

| R | Mites | | Mosquitoes | | Tobacco Budworms | | Cabbage Loopers | | Armyworms | | Mexican Bean Beetles | | Potato Beetles | |
|---|---|---|---|---|---|---|---|---|---|---|---|---|---|---|
| | ppm | hatch | ppm | hatch | ppm | hatch | ppm | hatch | ppm | hatch | ppm | hatch | ppm | hatch |
| —OCH(CH$_3$)$_2$ | 300 | + | 1.2 | 0 | 300 | 0 | 1000 | ± | 1000 | + | 1000 | ± | 1000 | |
| | 100 | + | .4 | | 100 | | 100 | 0 | 100 | 0 | 100 | 0 | 100 | |
| | 10 | 0 | .04 | | 10 | | 10 | | 10 | | 10 | | 10 | |
| | 1 | | | | 1 | | | | 1 | | | | 1 | |
| —CH—C$_2$H$_5$ \| CH$_3$ | 300 | + | 1.2 | 0 | 300 | + | 1000 | ± | 1000 | + | 1000 | + | 1000 | + |
| | 100 | + | .4 | | 100 | ± | 100 | 0 | 100 | ± | 100 | ± | 100 | + |
| | 10 | ± | .04 | | 10 | 0 | 10 | | 10 | | 10 | | 10 | 0 |
| | 1 | 0 | | | 1 | | | | 1 | | | | 1 | |
| (cyclopentyl) | 300 | + | 1.2 | + | 300 | + | 1000 | + | 1000 | + | 1000 | + | 1000 | + |
| | 100 | + | .4 | + | 100 | + | 100 | ± | 100 | + | 100 | ± | 100 | + |
| | 10 | + | .04 | 0 | 10 | + | 10 | 0 | 10 | + | 10 | ± | 10 | + |
| | 1 | 0 | | | 1 | 0 | | | 1 | | | 0 | 1 | |

Table I-continued
Ovicidal Activity of 1-Substituted-4-nitro-1H-Benzotriazoles vs. Galecron; Application rates are given in ppm Structure: 1-R-4-nitro-1H-benzotriazole (R on N1, NO$_2$ at position 4)

| R | Mites ppm | Mites hatch | Mosquitoes ppm | Mosquitoes hatch | Tobacco Budworms ppm | Tobacco Budworms hatch | Cabbage Loopers ppm | Cabbage Loopers hatch | Armyworms ppm | Armyworms hatch | Mexican Bean Beetles ppm | Mexican Bean Beetles hatch | Potato Beetles ppm | Potato Beetles hatch |
|---|---|---|---|---|---|---|---|---|---|---|---|---|---|---|
| —CH$_2$-cyclohexyl | 300<br>100<br>10<br>1 | +<br>0 | 1.2<br>.4<br>.04 | 0<br>+<br>+ | 300<br>100<br>10<br>1 | +<br>+<br>+<br>0 | 1000<br>100<br>10 | +<br>+ | 1000<br>100<br>10<br>1 | +<br>0 | 1000<br>100<br>10 | +<br>+ | 1000<br>100<br>10 | +<br>+<br>0 |
| -cyclohexenyl | 300<br>100<br>10<br>1 | 0 | 1.2<br>.4<br>.04 | +<br>±<br>0 | 300<br>100<br>10<br>1 | +<br>+<br>+<br>0 | 1000<br>100<br>10 | +<br>0 | 1000<br>100<br>10<br>1 | +<br>+<br>±<br>0 | 1000<br>100<br>10 | +<br>+ | 1000<br>100<br>10<br>1 | +<br>+<br>+ |
| —C(CH$_3$)$_3$ | 300<br>100<br>10<br>1 | +<br>+<br>+<br>0 | 1.2<br>.4<br>.04 | 0<br>+<br>+ | 300<br>100<br>10<br>1 | 0 | 1000<br>100<br>10 | + | 1000<br>100<br>10<br>1 | ± | 1000<br>100<br>10 | 0 | 1000<br>100<br>10<br>1 | ±<br>0<br>0 |
| Galecron | 300<br>100<br>10<br>1 | +<br>±<br>0 | 1.2<br>.4<br>.04 | 0<br>+<br>± | 300<br>100<br>10<br>1 | +<br>+<br>±<br>0 | 1000<br>100<br>10 | +<br>+ | 1000<br>100<br>10<br>1 | +<br>+<br>+<br>0 | 1000<br>100<br>10 | 0 | 1000<br>100<br>10 | 0<br>0<br>0 |

EXAMPLE 2

By the procedure of Example 1 the ovicidal activity of some of the substituted-1H-benzotriazole compounds is evaluated in comparison to Galecron on mosquito and tobacco budworm eggs and 2-spotted spider mite eggs and adults. The results obtained are given in Table II below.

The following ratings are used in Table II.
0 = 0 – 40% kill
5 = 41 – 80% kill
9 = 81 – 100% kill
Symbols: A = Adults, E = Eggs.

Table II
Ovicidal Activity of Benzotriazole Compounds vs. Galecron; Application rates are given in ppm Structure: 1-R-4-nitro-1H-benzotriazole

| R | Mosquito Egg Kill 1.2 ppm | Mosquito Egg Kill .4 ppm | Tobacco Budworm Egg Kill 300 ppm | Tobacco Budworm Egg Kill 100 ppm | Tobacco Budworm Egg Kill 10 ppm | Tobacco Budworm Egg Kill 1 ppm | 2-Spotted Spider Mite Kill 300 ppm | 2-Spotted Spider Mite Kill 100 ppm | 2-Spotted Spider Mite Kill 10 ppm | 2-Spotted Spider Mite Kill 1 ppm |
|---|---|---|---|---|---|---|---|---|---|---|
| C$_3$H$_7$(n) | 0 | | 0 | | | | A 9<br>E 9 | 9<br>0 | 0 | |
| C$_3$H$_7$(i) | 0 | | 9 | 0 | | | A 9<br>E 9 | 9<br>9 | 0<br>0 | |
| C$_4$H$_9$(n) | 9 | 0 | 9 | 9 | 9 | 0 | A 0<br>E 0 | | | |
| —CH(CH$_3$)—C$_2$H$_5$ | 0 | | 9 | 5 | 0 | | A 9<br>E 9 | 9<br>9 | 5<br>5 | 0<br>0 |
| —C(CH$_3$)$_3$ | 0 | | 0 | | | | A 0<br>E 9 | 0<br>9 | 0<br>9 | 0<br>0 |
| —C$_5$H$_{11}$(n) | 9 | 0 | 9 | 9 | 9 | 0 | A 0<br>E 0 | | | |
| CH$_2$CH$_2$CH(CH$_3$)$_2$ | 9 | 0 | 9 | 9 | 9 | 0 | A 0<br>E 0 | | | |
| cyclopentyl | 9 | 9 | 9 | 9 | 9 | 0 | A 9<br>B 9 | 0<br>9 | 0<br>9 | 0 |
| cyclohexyl | | | 9 | 9 | 0 | | A 9<br>E 5 | 0<br>0 | | |
| Cycloheptyl | 9 | 9 | 9 | 9 | 9 | 9 | A 9<br>E 9 | 0<br>9 | 0<br>0 | |
| Cyclooctyl | 9 | 0 | 9 | 9 | 9 | 0 | A 0<br>E 0 | | | |
| —CH$_2$-cyclohexyl | 0 | | 9 | 9 | 9 | 0 | A 0<br>E 9 | 0<br>0 | | |
| —CON(CH$_3$)$_2$;-7-NO$_2$ | 0 | | 0 | | | | A 9<br>E 9 | 9<br>9 | 0<br>0 | |

Table II-continued
Ovicidal Activity of Benzotriazole Compounds vs. Galecron;
Application rates are given in ppm

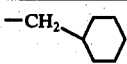

| | Mosquito Egg Kill | | Tobacco Budworm Egg Kill | | | | 2-Spotted Spider Mite Kill | | | |
|---|---|---|---|---|---|---|---|---|---|---|
| R | 1.2 ppm | .4 ppm | 300 ppm | 100 ppm | 10 ppm | 1 ppm | 300 ppm | 100 ppm | 10 ppm | 1 ppm |
| Galecron | 0 | | | | | | A 9 | 0 | | |
| | | | 9 | 9 | 5 | | E 9 | 9 | 0 | |

EXAMPLE 3

Evaluation of Ovicidal Activity of 1-Substituted-4-nitro-1H-benzotriazole compounds vs. Galecron Test solutions are prepared in 50% acetone - 50% water at 1000, 100 and 10 ppm concentrations of the compounds tested. Galecron is used as standard.

Cotton plants with one true leaf expanded are dipped in the solutions of the compounds tested. At the same time pieces of cheesecloth infested with about 100 0-24 hours old tobacco budworm eggs (*Heliothis virescens*) are dipped in the same solutions and placed on the treated leaf. After the plants and egg cloths are dried in a hood, they are held at 80° F. Tobacco budworms hatch after 3 days under these conditions. Estimates of hatch of budworms are made 3 days after infestation with eggs.

The results are given in Table III below:

Table III
Ovicidal Activity of 1-Substituted-4-nitro-1H-Benzotriazoles against Tobacco Budworm as Compared to Galecron

| R | Application Rate ppm | Treated leaves + eggs 0 hours |
|---|---|---|
| —CH₂⟨⟩ | 1000 | NH |
| | 100 | NH |
| | 10 | NH |
| ⟨⟩ | 1000 | NH |
| | 100 | NH |
| | 10 | NH |
| Galecron | 1000 | NH |
| | 100 | TH |
| | 10 | H |
| Control | — | H |

NH = No Hatch
TH = Trace Hatch
H = Normal Hatch

EXAMPLE 4

Evaluation of Residual Ovicidal Activity of 1-Substituted-4-nitro-1H-benzotriazole compounds against tobacco budworm eggs as compared to Galecron Test solutions are prepared at 1000 ppm concentration and cotton plants are treated as in Example 3. When dry, the plants are placed in 1 cubic foot screen cages, 1 plant per cage. Twenty 1-day old tobacco budworm moths of mixed sexes are released in each cage.

Eggs are first found on the plants 2 days after treatment and hatching of eggs begins the night of the 6th day after treatment, which is normal for this insect when held at 80° F.

Estimates of hatch are made and the data obtained are given in Table IV below.

TABLE IV
Residual Ovicidal Activity of 1-Substituted-4-nitro-1H-benzotriazoles at 1000 ppm against tobacco budworm eggs as compared to Galecron

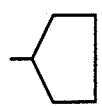

| R | 6 - Days |
|---|---|
|  | NH |
| | NH |
| Galecron Control | NH |
| | H |

NH = No hatch
H = Normal Hatch

EXAMPLE 5

Evaluation of Residual Activity of 1-Substituted-4-nitro-1H-benzotriazole compounds against P-resistant Spider Mite eggs and nymphs Test solutions are prepared at 1000 ppm and 100 ppm concentration and lima bean plants with 2 primary leaves are treated as in Example 3. P-resistant 2-spotted spider mites (*Tetranychus urticae*) are placed on the bean plants about 4 hours before treatment in the case of the 0 hour treatment so that eggs and leaves are both treated. In the case of the 1 hour, 1, 4 and 7 day post treatments, egg infestation is accomplished by placing about 100 adult mites on the treated leaves at the appropriate time after initial treatment. Plants are maintained at 80° F, 50% r.h. and observed 7 days after infestation for kill of eggs or of newly hatched nymphs. The data obtained are given in Table V below.

Table V

Residual Activity of 1-Substituted-4-nitro-1H-benzotriazoles
Against the Eggs and Nymphs of 2-Spotted Spider Mite (*Tetranychus urticae*)

| R | Application Rate ppm | Pre-infested 0 Hour | 1 Hour | 1 Day | 4 Days | 7 Days |
|---|---|---|---|---|---|---|
| —OCH(CH$_3$)$_2$ | 1000 | 100 E | 100 E | 100 E | 100 E | 100 E |
|  | 100 | 100 E | 88 E, 0 N | 0 E&N | 0 E&N | 0 E&N |
| —CH(CH$_3$)(C$_2$H$_5$) | 1000 | 100 E | 100 E | 100 E | 100 E | 100 E |
|  | 100 | 100 E | 100 E | 100 E | 100 E | 100 E |
| 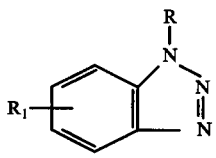 | 1000 | 100 E | 100 E | 100 E | 100 E | 100 E |
|  | 100 | 100 E | 100 E | 100 E | 100 E | 100 E |
| —C(CH$_3$)$_3$ | 1000 | 90 E, 100 N | 100 E | 100 E | 99 E | 100 E |
|  | 100 | 100 E | 87 E, 100 N | 86 E, 100 N | 75 E, 100 N | 50 E, 100 N |
| Control | — | 0 E&N | 0 E&N | 0 E&N | 0 E&N | 0 E&N |

Column header: % Kill of Eggs (E) and Nymphs (N) 7 Days Post Infestation; Infested Post Treatment E = Eggs of 2-Spotted Spider Mite
N = Nymphs of 2-Spotted Spider Mite

I claim:

1. A method for the control of insects and acarina comprising, contacting the eggs of the insects and acarina with an ovicidally effective amount of a compound of the formula:

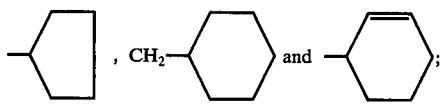

wherein R represents alkyl C$_3$–C$_8$ straight chain or branched, alkoxy C$_1$–C$_8$ straight chain or branched, cycloalkyl C$_3$–C$_8$, cycloalkenyl C$_5$–C$_6$, mono- or di-C$_1$–C$_3$ alkylcyclohexyl, cyclohexylmethyl, formyloxycyclohexyl, or —CONR$_2$R$_3$ wherein R$_2$ and R$_3$ represent hydrogen or alkyl C$_1$–C$_4$; and R$_1$ represents —NO$_2$ or —NCS.

2. The method according to claim 1, wherein R represents alkyl C$_3$–C$_5$ branched, alkoxy C$_1$–C$_3$ straight chain or branched, C$_4$–C$_6$ cycloalkyl, cycloalkenyl C$_5$–C$_6$, cyclohexylmethyl, —CON(CH$_3$)$_2$; and R$_1$ represents —NO$_2$ or —NCS.

3. The method according to claim 1, wherein R represents —C(CH$_3$)$_3$, —CH(CH$_3$)(C$_2$H$_5$)

and R$_1$ is 4-NO$_2$.

4. The method according to claim 2, wherein the compound is 1-sec-butyl-4-nitro-1H-benzotriazole.

5. The method according to claim 2, wherein the compound is 1-cyclopentyl-4-nitro-1H-benzotriazole.

6. The method according to claim 2, wherein the compound is 1-(cyclohexylmethyl)-4-nitro-1H-benzotriazole.

7. The method according to claim 2, wherein the compound is 1-(2-cyclohexen-1-yl)-4-nitro-1H-benzotriazole.

8. The method according to claim 1, wherein the compound is applied at a rate of from 0.14 kg per hectare to 5.60 kg per hectare.

9. The method according to claim 8, wherein the compound is applied at a rate of from 0.28 kg per hectare to 1.12 kg per hectare.

10. The method for the protection of plants against attack by insects and acarina comprising applying to the foliage of the plants an ovicidally, insecticidally or acaricidally effective amount of the compound 1-cyclopentyl-4-nitro-1H-benzotriazole.

11. A method for the protection of plants against attack by insects and acarina comprising applying to the foliage of the plants an ovicidally, insecticidally or acaricidally effective amount of the compound 1-(cyclohexylmethyl)-4-nitro-1H-benzotriazole.

12. A method for the protection of plants against attack by insects and acarina comprising applying to the foliage of the plants an ovicidally, insecticidally or acaricidally effective amount of the compound 1-(2-cyclohexen-1-yl)-4-nitro-1H-benzotriazole.

* * * * *